United States Patent [19]
Grushin

[11] Patent Number: 5,919,984
[45] Date of Patent: Jul. 6, 1999

[54] CATALYTIC PROCESS FOR THE SELECTIVE OXIDATION OF ORGANIC TERTIARY POLYPHOSPHINES TO PHOSPHINE MONOOXIDES

[76] Inventor: Vladimir Grushin, 1 A Congressional Dr., Greenville, Del. 19807

[21] Appl. No.: 09/062,462

[22] Filed: Apr. 17, 1998

[51] Int. Cl.[6] .................................................... C07F 9/53
[52] U.S. Cl. .............................. 568/14; 568/17; 556/13; 556/16; 556/18
[58] Field of Search .................. 568/14, 17; 556/13, 556/16, 18

[56] References Cited

U.S. PATENT DOCUMENTS 3,067,258  12/1962  Grayson .

OTHER PUBLICATIONS

R. W. Wegman et al., *Chem. Soc. Chem. Commun.*, 1891, 1987.
S. L. Brock et al., *Inorg. Chem.*, 30, 2138, 1991.
S. J. Berners–Price et al., *Inorg. Chem.*, 26, 3383, 1987.
M. R. Mason et al., *Organometallics*, 11, 2212, 1992.
F. Ozawa et al., *Chem. Lett.*, 2177, 1992.
CA:106:18696, abs of "Asimple synthesis and some synthetic applications of substituted phosphide and phosphinite anions" by Kabachnik, Synthesis (3) pp. 198–208, 1986.
CA::112:158360 abs of "Synthesis of vinyldiphenylsphosphine from diphenylphosphonic acid" by Bondarenko, Zh Obsch Khim 59(7), pp. 1533–1537, 1989.
CA:75:436318 abs of "Cyclopentadienyl (triphenylphosphine) ethylene rhodium and related compounds", by Graham, Inorg Chem 10(6) pp. 1165–1169, 1971.

*Primary Examiner*—Gary Geist
*Assistant Examiner*—Jean F Vollano

[57] ABSTRACT

This invention concerns a process for the selective mono oxidation of organic tertiary polyphosphines to phosphine monooxides. These monooxides are useful as ligands for transition metals in the formation of transition metal catalysts.

16 Claims, No Drawings

CATALYTIC PROCESS FOR THE SELECTIVE OXIDATION OF ORGANIC TERTIARY POLYPHOSPHINES TO PHOSPHINE MONOOXIDES

FIELD OF THE INVENTION

This invention concerns a process for the selective mono oxidation of organic tertiary polyphosphines to phosphine monooxides.

TECHNICAL BACKGROUND

Organic tertiary polyphosphine monooxides are useful as phosphorus ligands for transition metals in the formation of transition metal complexes for use as homogeneous catalysts in various carbonylation, hydrogenation, hydroformylation, homologation, and other reactions. Such uses have been reported by R. W. Wegman, et al., *Chem. Soc., Chem. Commun.*, 1987, 1891, and in U.S. Pat. Nos. 4,400,548 and 4,670,570.

The direct oxidation of tertiary polyphosphines using oxidants like hydrogen peroxide, aqueous bromine, organic peroxides, oxygen, and the like leads to non-selective reactions, resulting in the formation of complex mixes comprising the unchanged starting material, and its monooxidized, dioxidized, etc. derivatives which are formed in statistically expected admixtures. S. L. Brock and J. M. Mayer, *Inorg. Chem.* 1991, 30, 2138 report a 13% yield of the desired monooxide by the direct oxidation.

U.S. Pat. No. 4,429,161 discloses a two-step process for the preparation of tertiary polyphosphine monooxides. The process is described as highly selective and said to yield, potentially, a very pure product. The process involves the selective monoalkylation of a tertiary polyphosphine to a monophosphonium salt, followed by isolation, recovery and, optionally, purification of this intermediate and the subsequent alkaline hydrolysis of the monophosphonium salt to the polyphosphine monooxide.

S. J. Berners-Price et al., *Inorg. Chem.* 1987, 26, 3383, report the in situ formation of the monooxide derivative of 1,2-bis(diphenylphosphino)ethane by reaction of 1,2-bis (diphenylphosphino)ethane with a stoichiometric amount of copper(II) sulfate. The compound was observed and characterized spectroscopically but was not isolated.

M. R. Mason and J. G. Verkade, *Organometallics* 1992, 11, 2212, report the formation of a series of bis phosphine monooxides by the stoichiometric oxidation of the corresponding bis phosphines by palladium(II) chloride or platinum(II) chloride. F. Ozawa et al., *Chem. Lett.* 1992, 2177, report similar stoichiometric oxidation of a fully aromatic bis phosphine.

The process of the present invention concerns a one-step catalytic method for the selective monooxidation of organic tertiary polyphosphines.

SUMMARY OF THE INVENTION

This invention provides a process for the selective oxidation of organic tertiary polyphosphines of the structure:

$$R^1R^2P\text{---}Y\text{---}PR^3R^4$$

wherein
each of $R^1$, $R^2$, $R^3$, $R^4$, are selected independently from the group consisting of alkyl containing up to about 8 carbon atoms, substituted alkyl containing up to about 8 carbon atoms, aryl, including phenyl, substituted aryl, aralkyl, ring-substituted aralkyl, heteroaryl, substituted heteroaryl, cycloalkyl substituted cycloalkyl or any 2 or more of $R^1$ to $R^4$ are joined together to form one or more ring(s) and or bicyclic rings; and Y is a bidentate radical selected from the group consisting of $(CR^5R^6)_n$, where n is an integer from 1 to 4 and $R^5$ and $R^6$ are each selected from the group consisting of H, F, alkyl, containing up to about 8 carbon atoms, cycloalkyl, aryl, heteroaryl, aralkyl, vinyl and allyl or where $R^5$ and $R^6$ may be joined together to form a ring;

$(CR^5R^6)_pX(CR^5R^6)_q$, where p and q are, independently, integers from 1 to 3 and X is selected from the group consisting of O, S, SO, $SO_2$, $NR^5$, $N(O)R^5$, $[NR^5R^6]^+$, $NR^5NR^6$, N=N, $SiR^5R^6$, $GeR^5R^6$, $SnR^5R^6$, Hg, $TlR^5$;

cis-$CR^5$=$CR^6$;

cis-$CR^5R^6CR^5$=$CR^6CR^5R^6$;

$CR^5R^6CR^5R^6CR^5$=$CR^6$;

1,2-phenylene;

1,2-naphthylene, 2,3-naphthylene and 1,8-naphthylene;

2,2'-biphenylene;

2,2'-(1,1'-binaphthylene);

2,2'-$C_6H_4$---X---$C_6H_4$;

cyclopropanediyl;

1,1'-ferrocenylene;

1,2-ferrocenylene; and 1,2-carboranediyl ($C_2B_{10}H_{10}$); and wherein any of $R^1$ to $R^6$ and Y may, optionally, contain additional remote, unreactive tertiary phosphine groups, to form the corresponding phosphine monooxide comprising the steps of:

(a) contacting under oxidizing conditions said organic tertiary phosphine with an oxidant selected from the group consisting of olefinic precursors vicinally disubstituted with good leaving groups optionally in the presence of a catalytically effective amount of a metal catalyst selected from the group consisting of, palladium, platinum, silver, gold, rhodium, ruthenium, osmium, nickel, cobalt and iron or alternate salt forms or complexes thereof optionally in the presence of a promoter comprising a source of iodide ion, and, optionally, recovering the corresponding monooxide product.

DETAILED DESCRIPTION OF THE INVENTION

One of the most preferred embodiments of the present invention includes applying said process to phosphines of the structure $$R^1R^2P\text{---}Y\text{---}PR^3R^4$$

wherein
each of $R^1$, $R^2$, $R^3$, and $R^4$ are phenyl; and
Y is selected from the group consisting of $(CH_2)_n$, where n is an integer from 1 to 4, 1,1'-ferrocenylene and 2,2'-(1,1'-binaphthylene).

For sake of convenience this embodiment will be used in the illustrative equation below.

$$R^1R^2P\text{---}Y\text{---}PR^3R^4 + 2NaOH + BrCH_2CH_2Br \xrightarrow{Pd}$$

$$R^1R2P\text{---}Y\text{---}P(O)R^3R^4 + 2NaBr + CH_2=CH_2 + H_2O$$

The process of the present invention can be carried out under a variety of reaction conditions, for example, homogeneous, heterogeneous, biphasic, or phase-transfer conditions.

The process of the present invention is advantageously carried out in a solvent, a mixture of solvents, a biphasic mixture of solvents or under phase-transfer catalyst conditions. The reaction solvent can be any suitable organic solvent in which the starting material and the catalyst are sufficiently soluble to allow the reaction to proceed. Aprotic solvents are employed, e.g., hydrocarbons (benzene, toluene), ethers (ethyl ether, THF), and the like. Solvents which react with the reagents or deactivate the catalytically active species (e.g., carbon tetrachloride) are, generally, to be avoided. In some cases, however, as with 1,2-dichloroethane, the same material may function as both reagent and solvent. The most preferred solvents are dichloromethane and 1,2-dichloroethane. The amount of solvent used is not narrowly critical as long as an amount sufficient to dissolve all or a part of the reagents and catalytically active species is employed.

The reaction can proceed within a temperature range of about 0° C.–150° C. A preferred reaction temperature is in the range of 20° C.–100° C. and a most preferred range is 20° C.–80° C. Ambient temperatures are considered most economical. Temperatures up to the boiling point of the solvents are preferred.

Although the process may be conducted under ambient atmosphere, it is preferably carried out in an inert atmosphere such as nitrogen or argon, because under the described reaction conditions the phosphines can be oxidized with oxygen in a nonselective manner. Further, in view of the use of a flammable solvent, an inert atmosphere is favored.

The progress of the reaction can be successfully monitored by a variety of analytical techniques, such as thin-layer chromatography or $^{31}$P NMR.

The process is conveniently conducted at atmospheric pressure, but there are no critical limits on the pressure employed.

The process is customarily carried out with vigorous agitation as it is important that the catalyst be first mixed thoroughly with the substrate phosphine and solvent before the oxidant is added. Vigorously mixing the reaction mixture is crucial when the process is run under biphasic or phase-transfer conditions.

The ratio of catalyst to substrate can vary, with some illustrative ratios being 0.001, 0.002, and 0.005 (by weight). In general a range of from 0.001 to 0.050 is preferred. This upper limit is chosen not from process considerations, but from economic considerations.

A wide variety of complexes of certain metals are capable of catalyzing the process; in particular, soluble compounds of metals selected from the group consisting of palladium, platinum, silver, gold, rhodium, ruthenium, osmium and nickel, or alternate salt or complex forms of metals can be employed. Compounds of palladium and platinum are preferred with palladium being the most preferred.

The specific oxidant employed for the process of the present invention is selected from the group consisting of olefinic precursors vicinally disubstituted with good leaving groups. For example, the leaving groups may be chloride, bromide, iodide, tosylate, mesylate, triflate, carboxylate, etc. Exemplary oxidants are 1,2-dichloroethane, 1,2-diiodoethane 1,2-dibromopropane and 1,2-dibromoethane. 1,2-Dibromoethane is preferred. Stoichiometry requires 1 equivalent of oxidant per mole of phosphorous to be oxidized. In practice, 1.1 or more equivalents are employed.

Alternate suitable starting materials for the process of the present invention are those that contain more than one pair of tertiary phosphine groups provided that in each pair of tertiary phosphine groups the phosphorus atoms are separated by a "Y" linkage as defined above.

In certain cases, the catalytic monooxidation can be conducted in the presence of a promoter which accelerates the process and/or leads to higher conversions and better yields. The promoter is a compound that serves as a source of iodide ion. Sodium iodide or other available iodides can be used. It is to be understood, however, that with some other substrates good yields and selectivities for said monooxidation process can be achieved in the absence of any specific promoter.

The reaction is carried out in the presence of a base having an aqueous pH of greater than 7. Hydroxides or alkoxides are conveniently employed. Two or more equivalents of base should be present for each phosphorous oxidized. Aqueous sodium hydroxide is a convenient base for the reaction.

The monooxides of tertiary organic polyphosphines are easily isolated from the reaction mixture by common techniques.

By the phrase "additional, remote unreactive tertiary phosphine groups" is meant phosphine groups spatially separated from the other phosphine groups such that coordination of said remote phosphine groups to the same metal catalyst atom coordinated to the properly separated phosphine groups cannot occur. This spatial separation is defined as being greater than the spatial separation that results in the specified "Y" groups.

The compounds formed herein are useful as ligands for transition metals used in the formation of metal complexes which are useful as catalysts.

EXAMPLES

A series of organic and organometallic bisphosphine monooxides were prepared from various bidentate phosphines by following the general procedure described below. General information, yields, and selected spectral data are collected in Table 1. All reactions were conducted on a 0.8–50 g scale. In addition to the $^{31}$P NMR spectral data (Table 1), other spectral characteristics (including $^1$H and $^{13}$C NMR) of the tertiary organic polyphosphine monooxides were obtained.

A dry three-neck flask or a Schlenk-type flask equipped with a gas inlet, optionally, a condenser, and a magnetic stirring bar was flushed with nitrogen and subsequently charged with a tertiary bisphosphine, a catalyst, and a solvent. The mixture was stirred for 5–30 minutes, and then the oxidant (in admixture with a promoter, if required) was added. The resulting system was vigorously stirred under nitrogen at 20–80° C. The progress of the reactions was followed by monitoring the consumption of the phosphine starting material by thin layer chromatography or $^{31}$P NMR techniques. Upon completion of the reaction (90–100% conversion), the organic solution was filtered through a sorbent plug which was then washed with an organic solvent (s). The combined filtrates were reduced in volume with a rotary evaporator; the solid residues were washed with ether, separated, and dried under vacuum. The products were found to be spectroscopically pure without any additional purification. All reactions were carried out under nitrogen but were worked up in air.

Starting phosphines except BINAP were obtained from Organometallics Chemical Co., New Hampshire and used as received. BINAP was obtained from TCI, Japan. 1,2-Dibromoethane was obtained from Aldrich, Milwaukee, Wis.

Abbreviations employed:

dppm and dppmO: bis(diphenylphosphino)methane and its monooxide
dppe and dppeO: 1,2-bis(diphenylphosphino)ethane and its monooxide
dppp and dpppO: 1,3-bis(diphenylphosphino)propane and its monooxide
dppb and dppbO: 1,4-bis(diphenylphosphino)butane and its monooxide
dppfc and dppfcO: 1,1'-bis(diphenylphosphino)ferrocene and its monooxide
BINAP and BINAP(O): 2,2'-Bis(diphenylphosphino)-1,1'-binaphthyl and its monooxide

TABLE 1

| Tertiary Phosphine | Monooxide Product | Isolated Yield %* | $^{31}$P NMR, δ | J (P-P) Hz |
|---|---|---|---|---|
| $Ph_2PCH_2PPh_2$ | $Ph_2PCH_2P(O)Ph_2$ | 75–85 | −26.5 +29.8 | 50.5 |
| $Ph_2P(CH_2)_2PPh_2$ | $Ph_2P(CH_2)_2P(O)Ph_2$ | 78–87 | −11.5 +32.3 | 48.0 |
| $Ph_2P(CH_2)_3PPh_2$ | $Ph_2P(CH_2)_3P(O)Ph_2$ | 73–77 | −17.2 +32.0 | — |
| $Ph_2P(CH_2)_4PPh_2$ | $Ph_2P(CH_2)_4P(O)Ph_2$ | 80–83 | −15.5 +32.2 | — |
| $Ph_2PC_5H_4FeC_5H_4PPh_2$ | $Ph_2PC_5H_4FeC_5H_4P(O)Ph_2$ | 65 | −16.7 +28.5 | — |
| R–BINAP | R–BINAP(O) | 80 | −15.2 +27.0 | — |
| S–BINAP | S–BINAP(O) | 80 | −15.3 +28.1 | — |

*Multiple entries indicate results of multiple runs

Example 1 dppmO, 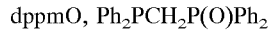

A mixture of palladium acetate (5 mg; 2.2×10$^{-2}$ mmol), dppm (2.00 g; 5.21 mmol), 1,2-dibromoethane (2.0 g; 10.64 mmol), and dichloromethane (10 mL) was stirred for 20 minutes. To this solution, aqueous NaOH (20% by weight; 6 mL) containing NaI (40 mg; 0.27 mmol) was added and the mixture was vigorously stirred under reflux for 4 hours. The organic phase was filtered through a silica plug which was then washed with CH$_2$Cl$_2$/AcOEt (3:1 by volume). The combined organic solutions were evaporated to dryness. The solid residue was dissolved in the minimum amount of boiling CH$_2$Cl$_2$, the warm solution was treated with ether (100 mL; portionwise) and left at room temperature for 2 hours. Slightly yellowish fluffy needles of spectroscopically and TLC pure dppmO were separated, washed with ether, and dried under vacuum. The yield was 1.53 g (74%). $^1$H NMR (CDCl$_3$, 20° C.), δ: 3.1 (d, 2H, J=12.7 Hz, CH$_2$); 7.1–7.9 (m, 20H, Ph). $^{31}$P NMR (CDCl$_3$, 20° C.), δ: −26.5 (d, 1P, J$_{P-P}$=50.5 Hz, PPh$_2$); 29.8 (d, 1P, J$_{P-P}$=50.5 Hz, P(O)Ph$_2$).

Example 2 dppeO, 

(a) Palladium acetate, (10 mg; 4.45×10$^{-2}$ mmol), dppe (4.00 g; 10.05 mmol) and 1,2-dibromoethane (2.85 g; 15.2 mmol) were dissolved in 1,2-dichloroethane (30 mL). To this solution, aqueous NaOH (10% by weight; 20 mL) was added and the biphasic mixture was vigorously stirred under reflux for 7 hours until the originally yellow mixture turned pale yellow or almost colorless. The organic phase was filtered through a silica plug which was then washed with 60 mL of CH$_2$Cl$_2$/AcOEt (5:3 by volume). The combined organic solutions were evaporated and treated with ether, causing precipitation of white crystals of dppeO which were washed with ether and dried under vacuum. The yield was 3.62 g (87%). $^1$H NMR (CDCl$_3$, 20° C.), δ: 2.3 (m, 4H, CH$_2$); 7.2–7.7 (m, 20H, Ph). $^{31}$P NMR (CDCl$_3$, 20° C.), δ: −11.5 (d, 1P, J$_{P-P}$=48 Hz, PPh$_2$); 32.3 (d, 1P, J$_{P-P}$=48 Hz, P(O)Ph$_2$).

(b) Palladium acetate (5 mg; 2.2×10$^{-2}$ mmol), dppe (5.00 g; 12.56 mmol), and 1,2-dibromoethane (3.6 g; 19.15 mmol) were dissolved in 1,2-dichloroethane (30 mL). To this solution, aqueous NaOH (12% by weight; 20 mL) was added and the biphasic mixture was vigorously stirred under reflux for 15 hours until the originally yellow mixture turned pale yellow or almost colorless. The product (4.29 g; 82%) was isolated as described above.

(c) Palladium acetate (50 mg; 22.3×10$^{-2}$ mmol) dppe (50.00 g; 125.6 mmol) and 1,2-dibromoethane (36 g; 191.5 mmol) were dissolved in 1,2-dichloroethane (200 mL). To this solution, aqueous NaOH (20% by weight; 125 mL) was added and the biphasic mixture was vigorously stirred under reflux for 21.5 hours until the originally yellow mixture turned pale yellow. The product (40.75 g; 78.3%) was isolated as described above.

Example 3 dpppO, 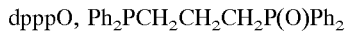

Palladium acetate (10 mg; 4.45×10$^{-2}$ mmol), dppp (5.00 g; 12.14 mmol), and 1,2-dibromoethane (3.4 g; 18.9 mmol) were dissolved in 1,2-dichloroethane (15 mL). To this solution, aqueous NaOH (20% by weight; 10 mL) was added and the biphasic mixture was vigorously stirred under reflux for 6 hours until the originally yellow mixture turned pale yellow. The organic phase was filtered through a silica column which was then washed with CH$_2$Cl$_2$/AcOEt (5:3 by volume) until the yellow band was about to come out. The combined organic solutions were evaporated to give a colorless oily residue. The oil was mixed with CH$_2$Cl$_2$ (2 mL) and ether (5 mL), and then treated with pentane (10 mL) and left for 1.5 hours. More pentane (50 ml) was added, and in 2 hours the fluffy white needles of dpppO were separated and dried under vacuum. The yield was 3.80 g (73%). $^1$H NMR (CDCl$_3$, 20° C.), δ: 1.8 (m, 2H, CH$_2$); 2.2 (m, 2H, CH$_2$); 2.4 (m, 2H, CH$_2$); 7.2–7.7 (m, 20H, Ph). $^{31}$P NMR (CDCl$_3$, 20° C.), δ: −17.2 (s, 1P, PPh$_2$); 32.0 (s, 1P, P(O)Ph$_2$).

Example 4 dppbO, 

A mixture of palladium acetate (10 mg; 4.45×10$^{-2}$ mmol), dppb (4.00 g; 9.4 mmol), 1,2-dibromoethane (3.6 g; 19.15 mmol), and dichloromethane (10 mL) was stirred for 30 minutes. To this suspension, aqueous NaOH (20% by weight; 10 mL) was added and the mixture was vigorously stirred at room temperature for 3 days. Dichloromethane (30 mL) was added, the organic phase was filtered through a silica plug which was then washed with 80 mL of $CH_2Cl_2$/AcOEt (5:3 by volume). The combined organic solutions were evaporated to dryness. The solid residue was dissolved in boiling $CH_2Cl_2$ (ca. 30 mL) and the solution was treated with ether (100 mL; portionwise) and left at room temperature for 2 hours. Well-shaped, colorless crystals were separated, washed with ether, and dried under vacuum. The yield was 3.33 g (80%). $^1$H NMR (CDCl$_3$, 20° C.), δ: 1.5 (m, 2H, CH$_2$); 1.7 (m, 2H, CH$_2$); 2.0 (m, 2H, CH$_2$); 2.2 (m, 2H, CH$_2$); 7.2–7.8 (m, 20H, Ph). $^{31}$P NMR (CDCl$_3$, 20° C.), δ: −15.5 (s, 1P, PPh$_2$); 32.2 (s, 1P, P(O)Ph$_2$).

Example 5 dppfcO Ph$_2$PC$_5$H$_4$FeC$_5$H$_4$P(O)Ph$_2$

A solution of NaOH (1.5 g; 37.5 mmol) and NaI (50 mg; 0.3 mmol) in water (6 mL) was added to a solution of dppfc (2.05 g; 3.7 mmol), Pd(OAc)$_2$, (10 mg; 4.45×10$^{-2}$ mmol), and 1,2-dibromoethane (2.0 g; 10.6 mmol) in dichloromethane (8 mL). This mixture was vigorously stirred under reflux (N$_2$) for 23.5 hours (TLC control). At this point the organic layer contained dppfcO as the main product and small amounts of dppfc, [(dppfc)PdI$_2$], C$_5$H$_5$FeC$_5$H$_4$P(O)PPh$_2$, and dppfcO$_2$. The organic phase was separated and evaporated. The dark residue was placed on a silica column which was then washed first with CH$_2$Cl$_2$ and then with CH$_2$Cl$_2$/AcOEt (5:3 by volume). Evaporation of the main fraction gave dppfcO which was washed with cold ether (2×5 mL), pentane (2×5 mL), and dried under vacuum. The yield was 1.36 g (65%). $^1$H NMR (CDCl$_3$, 20° C.) δ: 4.0 (m, 2H, Cp); 4.2 (m, 2H, Cp); 4.4 (m, 2H, Cp); 4.6 (m, 2H, Cp); 7.1–7.7 (m, 20H, Ph). $^{13}$C NMR (CDCl$_3$, 20° C.) δ: 72.9 (s, C$_5$H$_4$); 73.0 (s, C$_5$H$_4$); 73.1 (s, C$_5$H$_4$); 73.2 (s, C$_5$H$_4$); 73.3 (d, J$_{P-C}$=1.7 Hz, C$_5$H$_4$); 73.5 (d, J$_{P-C}$=1.7 Hz, C$_5$H$_4$); 128.2 (d, J$_{P-C}$=11.0 Hz, m-C$_6$H$_5$PCp); 128.4 (d, J$_{P-C}$=16.7 Hz, m-C$_6$H$_5$P(O)Cp); 131.3 (s, p-C$_6$H$_5$PCp); 131.4 (s, p-C$_6$H$_5$P(O)Cp); 131.4 (d, J$_{P-C}$=9.7 Hz, o-C$_6$H$_5$PCp); 133.4 (d, J$_{P-C}$=19.7 Hz, o-C$_6$H$_5$P(O)Cp); 134.5 (d, J$_{P-C}$=105.6 Hz, q-C$_6$H$_5$PCp); 138.8 (d, J$_{P-C}$=10.8 Hz, q-C$_6$H$_5$P(O)Cp). $^{31}$ NMR (CDCl$_3$, 20° C.) δ: −16.7 (s, 1P, CpPPh$_2$); 28.5 (s, 1P, CpP(O)Ph$_2$). Anal. Calcd for C$_{68}$H$_{58}$Fe$_2$O$_3$P$_4$ (C$_{34}$H$_{28}$FeOP$_2$.0.5H$_2$O): C, 70.5; H, 5.0. Found: C, 70.7; H, 5.0.

Example 6

BINAP(O) (R) or (S)

Palladium acetate (4 mg; 1.8×10$^{-2}$ mmol), BINAP (0.80 g, 1.29 mmol), and 1,2-dibromoethane (1.0 g; 5.3 mmol) were dissolved in dichloromethane (5 mL). Upon addition of aqueous NaOH (4.5% by weight; 6 mL) to this solution the organic phase immediately turned cherry red. After stirring the mixture at room temperature for 2 days the conversion reached was ca. 60–70%. More aqueous alkali (0.4 g of NaOH in 1.5 mL of water) was added and the mixture was stirred under reflux for 23 hours. At this point, only traces of the unreacted BINAP were detected in the organic phase (TLC). The dichloromethane layer was filtered through a silica plug which was then washed with dichloromethane. The combined organic solutions were evaporated and the oily residue was treated with ether (30 mL) and left at −17°

C. overnight. Large, colorless crystals of BINAP(O) were separated, washed with ether and dried under vacuum. The yield was 0.660 g (80%). $^{31}$P NMR (CDCl$_3$, 20° C.) δ: −15.3 (s, 1P, PPh$_2$); 28.1 (s, 1P, P(O)Ph$_2$).

What is claimed is:

1. A process for the selective oxidation of organic tertiary polyphosphines of the structure:

R$^1$R$^2$P—Y—PR$^3$R$^4$ wherein each of R$^1$, R$^2$, R$^3$, R$^4$, are selected independently from the group consisting of alkyl containing up to about 8 carbon atoms, substituted alkyl containing up to about 8 carbon atoms, aryl, including phenyl, substituted aryl, aralkyl, ring-substituted aralkyl, heteroaryl, substituted heteroaryl, cycloalkyl, substituted cycloalkyl, or any 2 or more of R$^1$ to R$^4$ are joined together to form one or more ring(s) and or bicyclic rings; and Y is a bidentate radical selected from the group consisting of (CR$^5$R$^6$)$_n$, where n is an integer from 1 to 4 and R$^5$ and R$^6$ are each selected from the group consisting of H, F, alkyl, containing up to about 8 carbon atoms, cycloalkyl, aryl, heteroaryl, aralkyl, vinyl and allyl or where R$^5$ and R$^6$ may be joined together to form a ring;

(CR$^5$R$^6$)$_p$X(CR$^5$R$^6$)$_q$, where p and q are, independently, integers from 1 to 3 and X is selected from the group consisting of O, S, SO, SO$_2$, NR$^5$, N(O)R$^5$, [NR$^5$R$^6$]$^+$, NR$^5$NR$^6$, N=N, SiR$^5$R$^6$, GeR$^5$R$^6$, SnR$^5$R$^6$, Hg, TlR$^5$;

cis-CR$^5$=CR$^6$;

cis-CR$^5$R$^6$CR$^5$=CR$^6$CR$^5$R$^6$;

CR$^5$R$^6$CR$^5$R$^6$CR$^5$=CR$^6$;

1,2-phenylene;

1,2-naphthylene, 2,3-naphthylene and 1,8-naphthylene;

2,2'-biphenylene;

2,2'-(1,1'-binaphthylene);

2,2'-C$_6$H$_4$—X—C$_6$H$_4$;

cyclopropanediyl;

1,1'-ferrocenylene;

1,2-ferrocenylene; and 1,2-carboranediyl (C$_2$B$_{10}$H$_{10}$); and wherein any of R$^1$ to R$^6$ and Y optionally contains additional remote, unreactive tertiary phosphine groups, to form the corresponding phosphine monooxide comprising the steps of:

(a) contacting under oxidizing conditions said organic tertiary phosphine substrate with an oxidant selected from the group consisting of olefinic precursors vicinally disubstituted with good leaving groups selected from the group consisting of chloride, bromide, iodide, tosylate, mesylate, triflate and carboxylate, in the presence of a catalytically effective amount of a metal catalyst selected from the group consisting of, palladium, platinum, silver, gold, rhodium, ruthenium, osmium, nickel, cobalt and iron or alternate salt forms or complexes thereof optionally in the presence of a promoter comprising a source of iodide ion, and, optionally, recovering the corresponding monooxide product.

2. The process of claim 1 having an organic tertiary polyphosphine wherein:

each of R$^1$, R$^2$, R$^3$, and R$^4$ are phenyl; and

Y is selected from the group consisting of (CH$_2$)$_n$, where n is an integer from 1 to 4, 1,1'-ferrocenylene and 2,2'-(1,1'-binaphthylene).

3. The process claim 1 carried out in the presence of an aprotic solvent.

4. The process of claim 3 wherein the solvent is 1,2-dichloroethane or dichloromethane.

5. The process of claim 1 wherein the reaction temperature is in the range of 0° C.–150° C.

6. The process of claim 1 wherein the percent of catalyst to substrate is from 0.1% to 5.0% by weight.

7. The process of claim 1 wherein the catalyst is selected from the group consisting of palladium and platinum.

8. The process of claim 7 wherein the catalyst is palladium.

9. The process of claim 1 wherein the oxidant is selected from the group consisting of 1,2-dichloroethane, 1,2-diiodoethane 1,2-dibromopropane and 1,2-dibromoethane.

10. The process of claim 9 wherein the oxidant is 1,2-dibromoethane.

11. The process of claim 1 conducted in the presence of a promoter that serves as a source of iodide ion.

12. The process of claim 1 wherein two or more equivalents of base are present for each phosphorus oxidized.

13. The process of claim 12 wherein the base is aqueous or solid sodium hydroxide.

14. The process of claim 1 carried out under biphasic conditions.

15. The process of claim 1 carried out under phase transfer catalysis conditions.

16. The process of claim 1 carried out under an inert atmosphere.

* * * * *